(12) United States Patent
Clarke et al.

(10) Patent No.: US 6,294,112 B1
(45) Date of Patent: Sep. 25, 2001

(54) RED COLORING HYPERCHROMIC 3H-NAPHTHO[2,1-B]PYRANS

(75) Inventors: David A. Clarke, Brighouse; Bernard Mark Heron, Yorkshire; Christopher David Gabbutt; John David Hepworth, both of Lancashire; Steven Michael Partington; Stephen Nigel Corns, both of Huddersfield, all of (GB)

(73) Assignee: James Robinson Limited, Huddersfield (GB)

( * ) Notice: Subject to any disclaimer, the term of this patent is extended or adjusted under 35 U.S.C. 154(b) by 0 days.

(21) Appl. No.: 09/402,355
(22) PCT Filed: Apr. 3, 1998
(86) PCT No.: PCT/GB98/00995
    § 371 Date: Dec. 16, 1999
    § 102(e) Date: Dec. 16, 1999
(87) PCT Pub. No.: WO98/45281
    PCT Pub. Date: Oct. 15, 1998

(30) Foreign Application Priority Data

Apr. 4, 1997 (GB) ................................. 9706939

(51) Int. Cl.[7] ............................ G02B 5/23; C07D 265/30; C07D 401/00; G02C 7/10
(52) U.S. Cl. ........................... 252/586; 544/106; 544/111; 544/124; 544/129; 544/141; 544/142; 544/143; 544/170; 546/187; 546/196; 546/200; 546/201; 548/440; 548/454; 351/163
(58) Field of Search .................. 252/586; 544/106, 544/111, 124, 129, 141, 142, 143, 170; 546/187, 196, 200, 201; 548/440, 454; 351/163

(56) References Cited

U.S. PATENT DOCUMENTS

| | | | |
|---|---|---|---|
| 5,458,815 | * 10/1995 | Knowles | 252/586 |
| 5,466,398 | * 11/1995 | Van Gemert | 252/586 |
| 5,552,090 | * 9/1996 | Van Gemert | 252/586 |
| 5,623,005 | * 4/1997 | Rickwood et al. | 252/586 |
| 5,637,262 | * 6/1997 | Van Gemert | 252/586 |
| 5,808,100 | * 9/1998 | Momoda et al. | 252/586 |
| 5,879,592 | * 3/1999 | Kumar | 252/586 |
| 6,022,496 | * 2/2000 | Kawabata et al. | 252/586 |
| 6,080,338 | * 6/2000 | Kumar | 252/586 |

FOREIGN PATENT DOCUMENTS 0250193    12/1987  (EP) .
9500866     6/1994  (WO) .

OTHER PUBLICATIONS

Chemical Abstracts, vol. 127, No. 3, 1997, Columbus, Ohio US; abstract No. 42375x, p. 1327.

* cited by examiner

Primary Examiner—Philip Tucker
(74) Attorney, Agent, or Firm—Stevens, Davis, Miller & Mosher, L.L.P.

(57) ABSTRACT

Red coloring hyperchromic compounds have the formula:

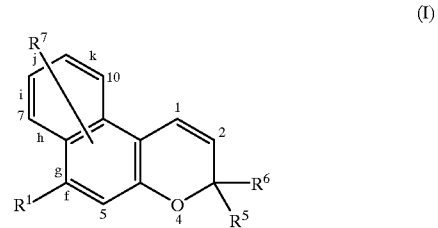

(I)

where $R^1$ is H, $NR^2R^3$, $OR^4$, $SR^4$ or $R^7$ wherein $R^2$ and $R^3$ are alkyl or carbocyclic groups or together with the nitrogen to which they are attached form a heterocyclic ring; $R^4$ is the same as $R^1$ or is alkyl, perhaloallyl, aryl or heteroaryl; $R^7$ is alkyl, haloalkyl, alkylthio, aryl, arylthio, heteroaryl, halogen, nitrile, carboxylate, ester, nitro, or a carbocyclic or heterocyclic ring fused to faces f, gh, i, j or k; and $R^5$ is a cyclic aminoaryl group, an indolinoaryl group, a tricyclic nitrogen heterocycle, or an unsaturated cyclic aminoaryl group.

20 Claims, No Drawings

RED COLORING HYPERCHROMIC 3H-NAPHTHO[2,1-B]PYRANS

The present invention relates o novel red colouring, hyperchromic 3H-naphtho[2,1-b]pyran photochromes and articles containing them.

Photochromism is a well-known physical phenomenon and has been detailed in "Photochromism: Molecules and Systems" Studies in Organic Chemistry, 40, Eds. H. Dürr and H. Bouas-Laurent, Elsevier, 1990.

The 3H-naphtho[2,1-b]pyran system is known to be capable or exerting a photochromic effect as described for example by Y. Hirshberg and E. Fischer, J. Chem. Soc., 1954, 3129 and R. Livingstone et al., J. Chem. Soc., 1958, 2422.

The basic 3H-naphtho[2,1-b]pyran structure is illustrated below:

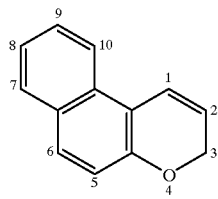

The 3H-naphtho[2,1-b]pyran system has been intensively studied, for example 3-spirocycloalkyl substituted 3H-naphtho[2,1-b]pyrans are described in U.S. Pat. No. 4,826,977 (1989), PCT WO 91/00861 (1991) and U.S. Pat. No. 5,532,361 (1996).

The photochromic properties of 3-alkyl or 3-cycloalkyl 3-aryl-3H-naphtho[2,1-b]pyrans have been described e.g. U.S. Pat. No. 4,818,096 (1989) and PCT WO 92/01959 (1992). However, 3,3-diaryl-3H-naphtho[2,1-b]pyrans have been shown to posses superior photochromic properties cf. the 3-spirocycloalkyl and 3-alkyl 3-aryl 3H-naphtho[2,1-b] pyrans, see for example PCT WO 97/06455 (1997) which describes 3-(4-biphenyl)-3-aryl-3H-naphtho[2,1b-]pyrans.

The type and position of substituents on the 3H-naphtho[2,1-b]pyran ring has been shown to be critical in controlling the colour, intensity and speed of the photochromic effect. The following patents illustrate such features: PCT WO 92/09593 (1992) describes 3,3-diaryl-3H-naphtho[2,1-b] pyrans which posses a substituent at the 5-position; PCT WO 95/00867 relates to 3,3-diaryl3H-naphtho[2,1-b]pyrans which contain an alkoxy or aryloxy substituent at the 8-position; U.S. Pat. No. 5,520,853 (1996) describes 3,3-diaryl-3H-naphtho[2,1-b]pyrans which contain an alkoxy or aryloxy function in the 6-position. Two closely related articles, PCT WO 94/22850 (1994) and U.S. Pat. No. 5,552,090 (1996), claim 3,3-diaryl-3H-naphtho[2,1-b] pyrans which have a cyclic amino function at the 6-position.

In addition to the effects of substituents located on the 3H-naphtho[2,1-b]pyrans ring, the presence of an ortho substituent on the 3-aryl function of 3,3-diaryl-3H-naphtho [2,1-b]pyran has been shown to influence the rate of bleaching of the photochromic effect, see U.S. Pat. No. 5,066,818 (1991) and PCT WO 95/00866 (1995).

We have now found that the presence of at least one 3(cyclic amino aryl) group imparts surprising and useful effects on the photochromism of 3H-naphtho[2,1-b]pyrans. In particular, this C-3 substituent not only provides photochromic materials with highly desirable rates of colouration and bleaching (fade) at ambient temperatures, but gives rise to materials which have a high induced optical density in the coloured form. Furthermore, by judicious choice of this C-3 group on the photochrome, the shade of the red colour which develops on irradiation can be fine tuned throughout the red region of the visible spectrum.

According to the present invention, there is provided a red-coloring photochromic naphtho[2,1-b]-pyran of the general formula (I)

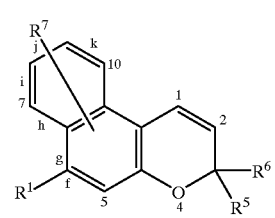

(I)

wherein $R^1$ represents either H or a group of the formula $-NR^2R^3$ or $-OR^4$ or $SR^4$ or $R^7$, and wherein when $R^1$ is $NR^2R^3$, each of $R^2$ and $R^3$, which may be the same or different, independently represents an alkyl group or a carobocyclic or heterocyclic group, or $R^2$ and $R^3$ taken together with the nitrogen atom to which they are attached represent a heterocyclic ring having one or more hetero atoms and which may be unsubstituted or carry at least one substituent selected from alkyl, aryl and heteroaryl groups; and wherein when $R^1$ is $OR^4$ or $SR^4$, the substituent $R^4$ represents an alkyl group, a perhaloalkyl group or an aryl or heteroaryl group;

$R^5$ represents a saturated cyclic aminoaryl substituent selected from:

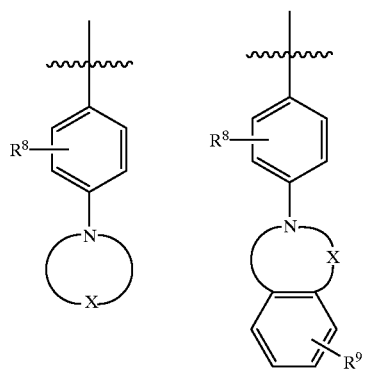

where the size of the saturated nitrogen-containing ring is from 3 to 30 atoms (inclusive of the N atom) and may incorporate one or more of the same or different heteroatoms or groups (X) where X is O, S, NH, N-alkyl, N-aryl or N-heteroaryl; or $R^5$ represents an indolinoaryl substituent of formula

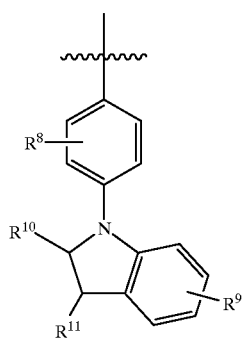

wherein $R^{10}$ and $R^{11}$ can, in addition to those functions specified below, be conjoined to form a ring of 5 to 8 atoms (including those which comprise the indoline ring), said ring being carbocyclic or heterocyclic where one or more of the ring carbon atoms is replaced by one or more of the same or different heteroatoms selected from O, S, or N, said nitrogen atom having either an H, alkyl, aryl or heteroaryl substituent; or $R^5$ may be of formula (II)

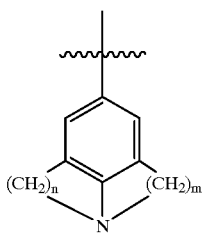

(II)

in which both m and n are integers between 2 and 5 and may be the same or different; or $R^5$ represents an unsaturated cyclic aminoaryl substituent selected from:

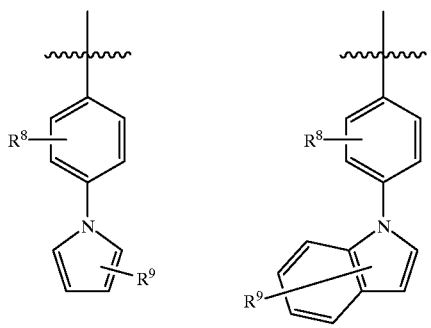

-continued

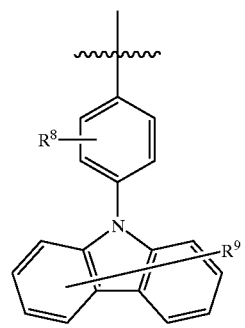

and wherein $R^6$ may be the same as or different from $R^5$, and when $R^6$ is different from $R^5$ it is selected from aryl, naphthyl and heteroaryl groups; and wherein $R^7$, $R^8$, $R^9$, $R^{10}$ and $R^{11}$ of which there may be multiples of either the same or different, may be selected from hydrogen, alkyl, haloalkyl, alkythio, aryl, arylthio, heteroaryl, halogen, nitrile, carboxylate, ester, nitro in additon to those substituents specified for $R^1$, or $R^7$ may represent a or heterocyclic ring fused to faces f, gh, i, j or k.

The photochromic properties exhibited by the novel pyran compounds of the present invention, namely those of a desirable rate of bleaching of the coloured form at ambient temperatures, a nigh induced optical density of the coloured form and control of the shade of red colour, render these compounds particularly useful as photochromic materials for incorporation into polymeric host materials so as to impart photochromic properties to the said polymeric host materials. Examples of applications of the polymeric host materials containing photochromic materials of the present invention include the manufacture of lenses for sunglasses and ophthalmic lenses, optical filters and windows for vehicles such as cars (including sunroofs), aircraft and ships and architectural uses e.g. windows for homes and for photochromic 'stained glass' windows. Additional uses may include incorporation into paints, inks and other like formulations.

The photochromic pyrans of the present invention may be incorporated into the 'plastic' host material by well established protocols for example as described in European patent no. 0254020 or U.S. Pat. No. 5,066,818.

The high induced optical density of the photochromic compounds of the present invention enables the amount of the photochromic materials required so as to impart a useful degree of photochromism to a polymeric host material or to a solution to be greatly reduced, thereby enabling a considerable saving of synthetic effort and cost. Furthermore, the use of reduced quantities of the photochromic materials of the present invention has the bonus that there is a consequent reduction in any undersirable colour that the photochromic materials may impart in the bleached state, either by way of inherent colour of the material itself or by the formation of coloured fatigue/degradation products through use of the photochromic material.

Typical host materials are polymer materials, preferably optically clear materials, such as polymers of polyol (allyl carbonate)-monomers, polyacrylates such as polymethylmethacrylates, cellulose acetate cellulose triacetate, cellulose acetate propionate cellulose acetate butyrate, poly(vinyl acetate), poly(vinyl alcohol), polyurethanes, polycarbonate, polyethylene terephthalate, polystyrene, poly(triethyleneglycol dimethylacrylate), poly(diethyleneglycol bis(allyl carbonate)) and various copolymer mixes.

The naphtho[2,1-b]pyrans of the present invention may be prepared by a general method which is based on the following, reaction scheme:

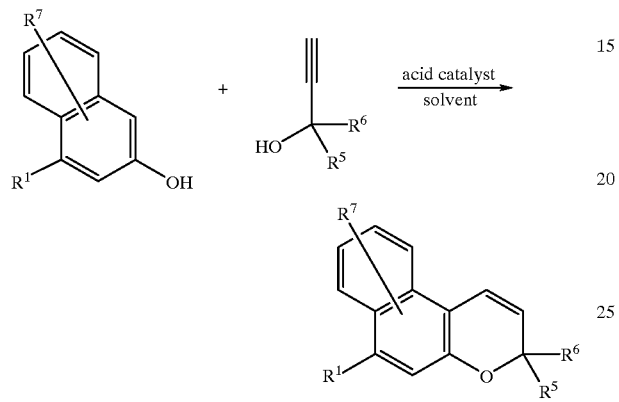

This general synthetic methodology has been described in detail, for example, by L. Merlini in "Advances in Heterocyclic Chemistry", 1975, vol. 18, page 159, and by R. Guglielmetti in "Photochromism: Molecules and systems," Studies in Organic Chemistry 40, chap. 8, Eds. H Dürr and H. Bouas-Laurent, Elsevier, 1990, and also in several patent documents, for example, WO 94/22850 and U.S. Pat. No. 5,520,853 (1996). The synthesis of the propargyl alcohols shown in the scheme above are obtained in a known manner, for example, T. F. Rutledge in 'Acetylenic Compounds,' Reinhold, New York, 1968.

The amino substituted benzophenones required for the synthesis of the propargyl alcohols are either commercially available or obtained by documented procedures involving a nucleophilic aromatic substitution of a halide ion from a halogeno benzophenone by a cyclic secondary amine. Nucleophilic aromatic substitution reactions have been documented see for example: Topics in Current Chemistry, 1975, 59, 33–64; Chimia, 1980, 34, 1–11; Accounts of Chemical Research, 1978, 11, 147–52.

The 2-naphthols and related hydroxy compounds are either commercially available or obtained by known synthetic methods, or derived from such methods see for example WO 94/22850.

The acid catalyst may be selected from acidic alumina (Brockmann 1), acetic acid, trifluoroacetic acid, aryl or alkyl sulfonic acids, silica, clays (e.g. montmorillionite, tonsil) or acidic exchange resins.

Organic solvents frequently employed for the reaction include benzene, toluene, xylene and relatively high boiling alkanes.

In order that the invention may be more fully understood, the following Examples are given by way of illustration only.

EXAMPLE 1

6-Morpholino-3(4-morpholinophenyl)-3-phenyl-3H-naphtho [2,1-b]pyran

A solution of 4-morpholino-2-naphthol (1.5 g, 6.5 mmol) and 1(4-morpholinophenyl)-1-phenylprop-2-yn-1-ol (1.92 g, 6.5 mmol) in toluene (65 cm$^3$) containing acidic alumina (Brockmann 1), (4.0 g) was refluxed for 60 minutes. The cooled solution was filtered and the alumina was washed well with EtOAc (200 cm$^3$). Removal of the solvent from the filtrate gave an oil which solidified on standing at room temperature. Recrystallisation from EtOAc/hexane gave 6-morpholino-3(4-morpholinophenyl)-3-phenyl-3H-naphtho[2,1-b]pyran (yield=2.4 g, theoretical yield=3.3 g 73%, m.p.=187–188° C. (uncorrected), $\lambda_{max}$ in toluene=469 nm, i.e. red-orange).

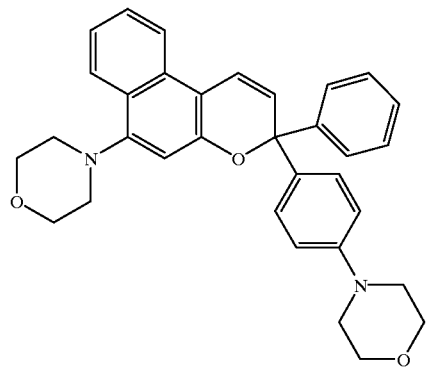

EXAMPLES 2–5

Using an identical protocol the following 3H-naphtho[2,1-b]pyrans were obtained.

(2) 6-Morphonlino-3(4-piperidinophenyl)-3-phenyl-3H-naphtho [2,1-b]pyran from 4-morpholino-2-naphthol and 1-phenyl-1-(4-piperidinophenyl)-prop-2-yn-1-ol (yield=1.76 g, theoretical yield=2.19 g 80% after recrystallisation from EtOAc and hexane, m.p.=170.5–172° C. (uncorrected), $\lambda_{max}$ in toluene=485 nm, i.e. red-orange).

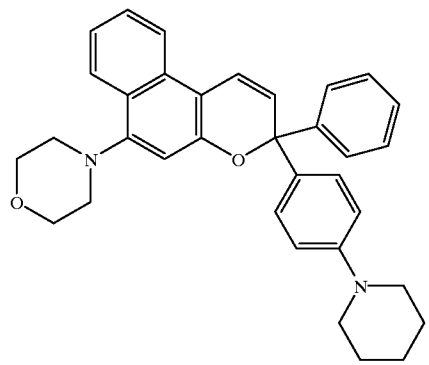

(3) 3(4-Methoxyphenyl)-6-morpholino-3(4-piperidinophenyl)-3H-naphtho-[2,1-b]pyran from 4-morpholino-2-naphthol and 1-(4-methoxyphenyl)-1-(4-piperidinophenyl)-prop-2-yn-1-ol (yield=1.74 g, theoretical yield=2.32 g 75% after recrystallisation from EtOAc, hexane and ethanol, m.p.=247–249° C. (uncorrected), $\lambda_{max}$ in toluene=489 nm, i.e. red-orange).

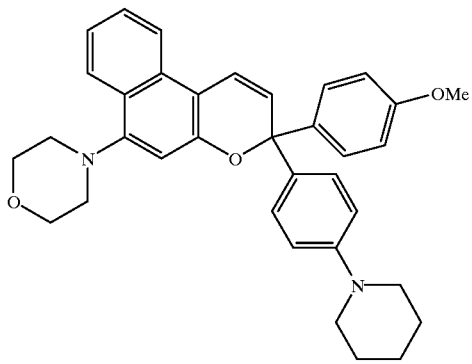

(4) 6-Morpholino-3(4-pyrrolidinophenyl)-3-phenyl-3H-naphtho[2,1-b]pyran from 4-morpholino-2-naphthol and 1-phenyl-1(4-pyrrolidinophenyl)-prop-2-yn-1-ol (yield= 1.4 g, theoretical yield=2.13 g 66% after recrystallisation from (uncorrected), $\lambda_{max}$ in toluene=513 nm, i.e. red).

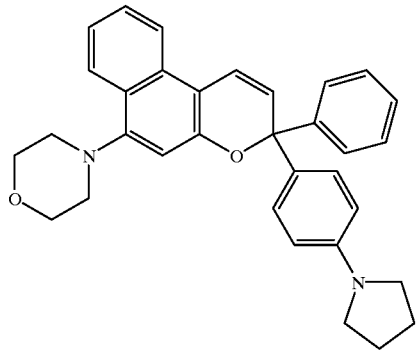

(5) 3(4-Morpholinophenyl)-3-phenyl-3H-naphtho[2,1-b]pyran from 2-naphthol and 1(4-morpholinophenyl)-1-phenylprop-2-yn-1-ol (yield=71% after recrystallisation from EtOAc and hexane, m.p.=186–187° C. (uncorrected), $\lambda_{max}$ in toluene=500 nm, i.e. red).

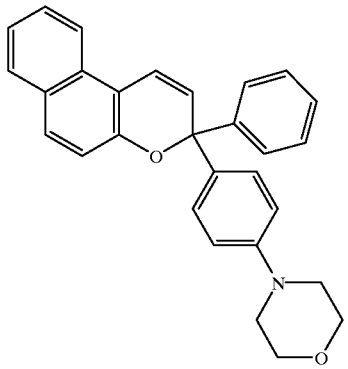

EXAMPLE 6 and 7

By way of comparison the following were prepared. These materials exhibited a yellow colour and fall outside the scope of the accompanying claims.

(6) 3,3-Di(4-methoxyphenyl-6-morpholino-3H-naphtho[2,1-b]pyran from 4-morpholino-2-naphthol and 1,1-di(4-methoxyphenyl)-prop-2-yn-1-ol (m.p.=210–212° C. (uncorrected), $\lambda_{max}$ in toluene=447 nm).

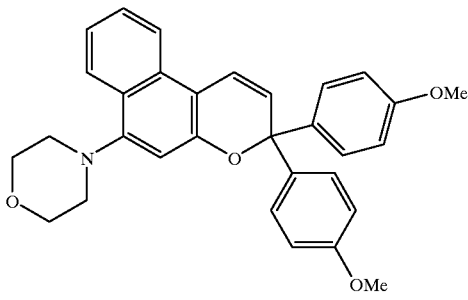

(7) 3,3-Diphenyl-3H-naphtho[2,1-b]pyran from 2-naphthol and 1,1-diphenylprop-2-yn-1-ol (m.p.=162–164° C. (uncorrected), $\lambda_{max}$ in toluene=430 nm).

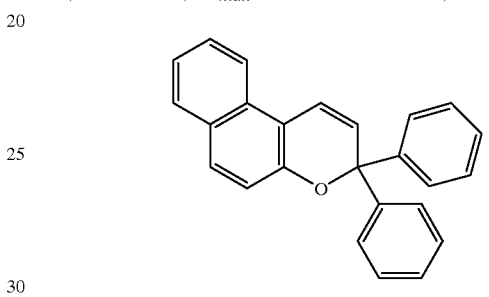

EXAMPLE 8

Pyrans of the invention were mixed with polymers to make compositions of the invention. For example, polyurethane compositions were made by mixing the pyran with the monomers and then polymerising. Coloured polyethylene and polypropylene compositions can be made by blending the pyran with the respective polymer, and then extruding. The amount of pyran can vary widely but normally an amount of from 0.1 to 0.3% by weight of the composition is used.

What is claimed is:

1. A red coloring photochromic naptho[2,1-b]-pryan of the general formula (I)

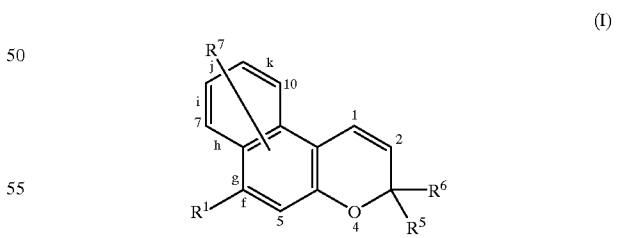

(I)

wherein $R^1$ represents either H or a group of the formula —$NR^2R^3$ or —$OR^4$ or $SR^4$ or $R^7$, and wherein when $R^1$ is $NR^2R^3$, each of $R^2$ and $R^3$, which may be the same or different, independently represents an alkyl group or a carobocyclic or heterocyclic group, or $R^2$ and $R^3$ taken together with the nitrogen atom to which they are attached represent a heterocyclic ring having one or more hetero atoms and which may be unsubstituted or carry at least one substituent selected from alkyl, aryl and heteroaryl groups;

and wherein when $R^1$ is $OR^4$ or $SR^4$, the substituent $R^4$ represents an alkyl group, a perhaloalkyl group or an aryl or heteroaryl group, $R^5$ represents a saturated cyclic aminoaryl substituent selected from:

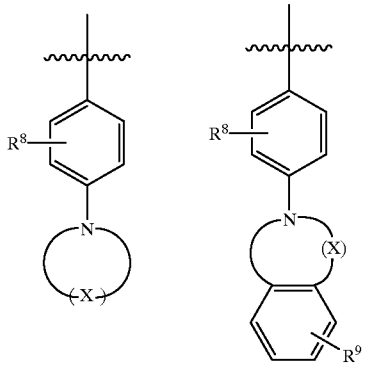

where the size of the saturated nitrogen-containing ring is from 3 to 30 atoms inclusive of the N atom and optionally may incorporate one or more of the same or different heteroatoms or groups (X) where X is O, S, NH, N-alkyl, N-aryl or N-heteroaryl; or $R^5$ represents an indolinoaryl substitutent of the formula

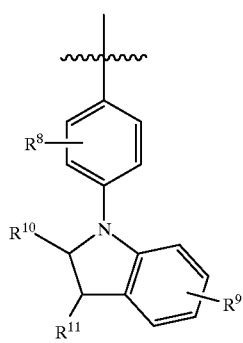

wherein $R^{10}$ and $R^{11}$ can, in addition to those functions specified below, be conjoined to form a ring of 5 to 8 atoms including those which comprise the indoline ring, said ring being carbocyclic or heterocyclic where one or more of the ring carbon atoms is replaced by one or more of the same or different heteroatoms selected from O, S, or N, said nitrogen atom having either an H, alkyl, aryl or heteroaryl substituent; or $R^5$ may be of formula (II)

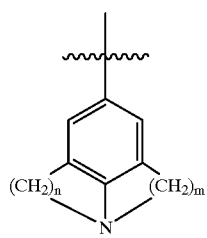

(II)

in which both m and n are integers between 2 and 5 and may be the same or different; or $R^5$ represents an unsaturated cyclic aminoaryl substituent selected from:

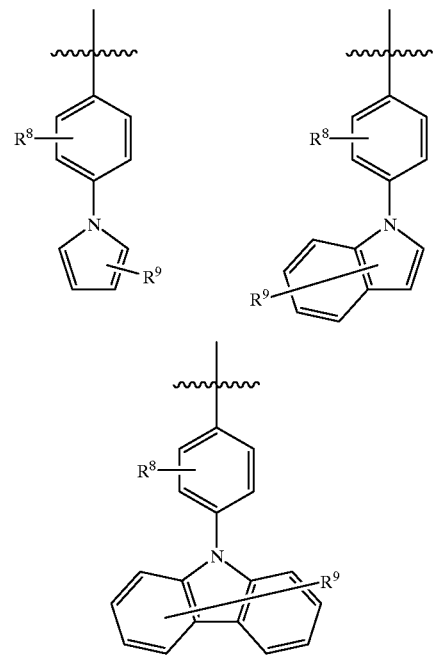

and wherein $R^6$ may be the same as or different from $R^5$, and when $R^6$ is different from $R^5$ it is selected from aryl and heteroaryl groups; and wherein $R^7$, $R^8$, $R^9$, $R^{10}$ and $R^{11}$ of which there may be multiples of either the same or different, may be selected from hydrogen, alkyl, haloalkyl, alkythio, aryl, arylthio, heteroaryl, halogen, nitrile, carboxylate, ester, nitro in addition to those substituents specified for $R^1$, or $R^7$ may represent a heterocyclic ring fused to faces f, g, h, i, j or k.

2. A naphthopyran compound according to claim 1, wherein the $R^1$ substituent is a piperidino group.

3. A naphthopyran compound according to claim 1, wherein the $R^1$ substituent is a morpholino group.

4. A naphthopyran compound according to claim 1, wherein the $R^1$ substituent is a N-alkylpiperazino group.

5. A naphthopyran compound according to claim 1, wherein the $R^1$ substituent is a N-indolino group.

6. A naphthopyran compound according to claim 1, where the $R^5$ substituent is a 4-morpholinophenyl group, a 4-pyrrolidinophenyl group or a 4-(4-methylpiperazino) phenyl group, and $R^6$ substituent is a phenyl group, a 4-methoxyphenyl group, a 2,4-dimethoxyphenyl group, a 4-trifluoromethylphenyl group, 2-thienyl or 3-thienyl.

7. A naphthopyran compound according to claim 1, wherein m and n are both 3.

8. 6-morpholino-3(4-morpholinophenyl)-3-phenyl-3H-naphtho-[2,1-b]pyran.

9. 6-morpholino-3(4-piperidinophenyl)-3-phenyl-3H-naphtho-[2,1-b]pyran.

10. 6-morpholino-3(4-morpholinophenyl)-3(2-thienyl)-3H-naphtho-[2,1-b]pyran.

11. 3(4-methoxyphenyl)-6-morpholino-3(4-piperidinophenyl)-3H-naphtho-[2,1-b]pyran.

12. 6-morpholino-3(4-pyrrolidinophenyl)-3-phenyl-3H-naphtho-[2,1-b]pyran.

13. 6-morpholino-3(4-morpholinophenyl)-3(4-trifluoromethyl-phenyl)-3H-naphtho[2,1-b]pyran.

14. 3(4-morpholinophenyl)-3-phenyl-3H-naphtho[2,1-b]pyran.

15. 3(4-morpholinophenyl)-3-(4-methoxyphenyl)-3H-naphtho[2,1-b]pyran.

16. A method of making a red-coloring photochromic naphtho(2,1-b)pyran as defined in claim 1, which comprises reacting an acetylenic derivative of formula

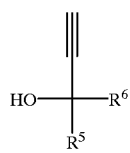

with a naphthalene derivative of formula

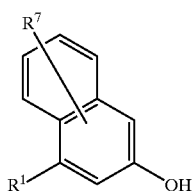

in the presence of an acid catalyst and a solvent.

17. A composition which comprises a polymeric material; and a naphtho(2,1-b)pyran as defined in claim 1.

18. A composition according to claim 17, wherein the polymeric material comprises a polyol(allyl carbonate) polymer; a polyacrylate; cellulose acetate, triacetate, acetate propionate or acetate butyrate; poly(vinyl acetate); poly(vinyl alcohol); polyurethane; polycarbonate; polyethylene terephthalate; polystyrene; poly-(triethyleneglycol dimethacrylate); poly(diethyleneglycol bis(allyl carbonate)).

19. An ophthalmic lens or sunglasses lens, an optical filter, a window, a paint or an ink which comprises a naphtho(2,1-b)pyran as claimed in claim 1.

20. The red-coloring photochromatic napthyl(2,1-b)-pyran of claim 1, in which when $R^6$ is different from $R^5$, $R^6$ is napthyl.

* * * * *